US011759588B2

(12) United States Patent
Isaza

(10) Patent No.: US 11,759,588 B2
(45) Date of Patent: Sep. 19, 2023

(54) ANTI-ASPHYXIA DESIGN FOR MECHANICAL VENTILATOR

(71) Applicant: KONINKLIJKE PHILIPS N.V., Eindhoven (NL)

(72) Inventor: Fernando Jose Isaza, Carlsbad, CA (US)

(73) Assignee: Koninklijke Philips N.V., Eindhoven (NL)

(*) Notice: Subject to any disclaimer, the term of this patent is extended or adjusted under 35 U.S.C. 154(b) by 347 days.

(21) Appl. No.: 17/159,200

(22) Filed: Jan. 27, 2021

(65) Prior Publication Data
US 2022/0001123 A1    Jan. 6, 2022

Related U.S. Application Data

(60) Provisional application No. 63/047,435, filed on Jul. 2, 2020.

(51) Int. Cl.
*A61M 16/00* (2006.01)
*A61M 16/20* (2006.01)
(Continued)

(52) U.S. Cl.
CPC ...... *A61M 16/022* (2017.08); *A61M 16/0051* (2013.01); *A61M 16/0066* (2013.01);
(Continued)

(58) Field of Classification Search
CPC .............. A61M 16/00; A61M 16/0051; A61M 16/0057; A61M 16/0066; A61M 16/0069;
(Continued)

(56) References Cited

U.S. PATENT DOCUMENTS 6,520,180 B1 * 2/2003 Sahmkow ......... A61M 16/0069
128/204.22
6,668,824 B1 12/2003 Doyle
(Continued)

FOREIGN PATENT DOCUMENTS

EP    3552648 A1    10/2019
FR    3040886 A1    3/2017
JP    4031403 B2    12/2007

OTHER PUBLICATIONS

International Search Report for PCT/EP2021/060195 filed Apr. 20, 2021.

*Primary Examiner* — Joseph D. Boecker
(74) *Attorney, Agent, or Firm* — Daniel H. Brean; Andrew M. Gabriel

(57) ABSTRACT

A ventilator system, comprising: an inhalation pathway comprising an ambient air inlet, a bi-directional emergency valve, and a dynamic blower; and an exhalation pathway comprising a bi-directional exhalation valve and an exhalation port; wherein when a blockage occurs in the inhalation pathway, ambient air can be drawn from the exhalation port and through the bi-directional exhalation valve, and during exhalation exhalant exits the ventilator through the bi-directional exhalation valve and the exhalation port; wherein when a blockage occurs in the exhalation pathway, inhalant is delivered by the dynamic blower, and during exhalation the dynamic blower lowers its speed or stops and the exhalant exits the ventilator through the bi-directional emergency valve, the dynamic blower, and the ambient air inlet.

20 Claims, 4 Drawing Sheets

(51) Int. Cl.
  *A61M 16/12* (2006.01)
  *A61M 16/08* (2006.01)
  *A61M 16/10* (2006.01)

(52) U.S. Cl.
  CPC ...... *A61M 16/024* (2017.08); *A61M 16/0883* (2014.02); *A61M 16/125* (2014.02); *A61M 16/20* (2013.01); *A61M 16/202* (2014.02); *A61M 16/203* (2014.02); *A61M 16/204* (2014.02); *A61M 16/205* (2014.02); *A61M 2016/0027* (2013.01); *A61M 2016/0039* (2013.01); *A61M 2016/0042* (2013.01); *A61M 2016/1025* (2013.01); *A61M 2202/0208* (2013.01); *A61M 2205/3334* (2013.01); *A61M 2205/3337* (2013.01)

(58) Field of Classification Search
  CPC .............. A61M 16/022; A61M 16/024; A61M 16/0883; A61M 16/125; A61M 16/203; A61M 16/204; A61M 16/205; A61M 2016/0027; A61M 2016/0039; A61M 2016/0042
  See application file for complete search history.

(56) References Cited

U.S. PATENT DOCUMENTS

| | | | |
|---|---|---|---|
| 9,616,192 | B2 | 4/2017 | Brambilla |
| 9,981,093 | B2 | 5/2018 | Chalvignac |
| 10,449,325 | B2 | 10/2019 | Kurtz |
| 2013/0276789 | A1* | 10/2013 | Garde ................ A61M 16/205 |
| | | | 128/205.24 |
| 2019/0275283 | A1* | 9/2019 | Adametz ........... A61M 16/0057 |
| 2019/0314596 | A1 | 10/2019 | Hall |
| 2019/0372369 | A1 | 12/2019 | Blunsden |
| 2021/0275762 | A1* | 9/2021 | Adametz ............. A61M 16/208 |
| 2021/0346638 | A1* | 11/2021 | Faulkner ............ A61M 16/024 |

* cited by examiner

ANTI-ASPHYXIA DESIGN FOR MECHANICAL VENTILATOR

CROSS-REFERENCE TO RELATED APPLICATIONS

This patent application claims the priority benefit under 35 U.S.C. § 119(e) of U.S. Provisional Application No. 63/047,435, filed on Jul. 2, 2020, and U.S. Provisional Application No. 63/016,345, filed on Apr. 28, 2020, the contents of which are herein incorporated by reference.

FIELD OF THE INVENTION

The present disclosure is directed generally to methods and systems for preventing asphyxia caused by blockages during mechanical ventilation of a patient.

BACKGROUND

Although ventilator design has grown increasingly complex and efficient, it still suffers from several significant limitations that can threaten the well-being of a ventilated subject. For example, a very simple event in the airflow pathway of the ventilator—namely a blockage (also called an obstruction or an occlusion)—can restrict or prevent the flow of air to the ventilated subject. Although the ventilator will detect the blockage and issue an alarm, the patient may not receive the necessary attention in time which may result in injury or death via asphyxiation. When an alarm is issued, a clinician must receive the alarm, arrive at the ventilator, identify the blockage, and fix the blockage in order for the subject to be properly ventilated again. If too much time elapses, the lack of oxygen can result in serious health consequences for the subject.

A blockage can occur several different ways in a ventilator. For example, if the blockage occurs in the tubing system section that conducts the gas to the subject, the subject will be able to exhale the gas in his/her lungs through the exhalation limb, the check valve, and the ventilator's exhalation port. However, when the subject attempts to inhale little or no gas is delivered to the patient due to the gas delivery path obstruction. This is further aggravated by the check valve blocking the gas flow from the environment towards his/her lungs. The subject will not be able to draw air from the environment since the check valve in the exhalation system will inhibit the flow of the gas from the environment towards the subject.

The blockage could alternatively occur in the tubing system between the subject's port and the exhalation gas outlet. This obstruction may be located in the tubing circuit portion, but may also occur due to a failure of the exhalation valve such that it remains closed. In this case, the gas in the subject's lungs cannot leave the system since the check valve located in the gas delivery port block all gas flow into the ventilator. Only gas flow towards the subject is allowed to flow, and the lungs remain inflated because the check valve in the exhalation port prevents the gas from leaving the tubing system since it blocks the path of the gas to the atmosphere. This leaves the subject inflated and with no possibility of gas exchange. In either of these cases, the subject will asphyxiate and die if left unattended. The subject may suffer an oxygen-deprivation injury if the clinician does not resolve the situation quickly enough.

SUMMARY OF THE INVENTION

Accordingly, there is a need for ventilators that allow a patient to breathe even in the occurrence of a blockage in either the gas delivery path or the gas return path, thereby preventing oxygen deprivation injuries or asphyxiation.

The present disclosure is directed to inventive methods and systems for enabling a flow of air to and from a ventilated patient in the event of a blockage in the gas delivery path or the gas return path. Various embodiments and implementations herein are directed to a ventilator system comprising an inhalation pathway with an ambient air inlet, a bi-directional emergency valve such as a safety valve or inspiratory hold valve, and a dynamic blower, and comprising an exhalation pathway with a bi-directional exhalation valve and an exhalation port. The exhalation pathway is configured such that when a blockage occurs in the inhalation pathway, during inspiration ambient air can be drawn by the patient from the exhalation port and through the bi-directional exhalation valve, and during exhalation exhalant exits the ventilator through the bi-directional exhalation valve and the exhalation port. The inhalation pathway is configured such that when a blockage occurs in the exhalation pathway, during inspiration inhalant is delivered to the patient by the dynamic blower, and during exhalation the dynamic blower lowers its speed or stops, and the exhalant exits the ventilator through the a bi-directional emergency valve, the dynamic blower, and the ambient air inlet.

Generally in one aspect, a ventilator system configured to enable breathing in the event of a blockage is provided. The ventilator system includes: (i) an inhalation pathway comprising an ambient air inlet, a bi-directional emergency valve, and a dynamic blower; and (ii) an exhalation pathway comprising a bi-directional exhalation valve and an exhalation port; wherein the exhalation pathway is configured such that when a blockage occurs in the inhalation pathway, during inspiration ambient air can be drawn by the patient from the exhalation port and through the bi-directional exhalation valve, and during exhalation exhalant exits the ventilator through the bi-directional exhalation valve and the exhalation port; and wherein the inhalation pathway is configured such that when a blockage occurs in the exhalation pathway, during inspiration inhalant is delivered to the patient by the dynamic blower, and during exhalation the dynamic blower lowers its speed or stops and the exhalant exits the ventilator through the bi-directional emergency valve, the dynamic blower, and the ambient air inlet.

According to an embodiment, the inhalation pathway further comprises a bi-directional ambient air flow sensor.

According to an embodiment, the inhalation pathway comprises an ambient air gas engine and a high-pressure gas engine. According to an embodiment, the high-pressure gas engine is a high-pressure oxygen source controlled by a proportional valve. According to an embodiment, the inhalation pathway further comprises a high-pressure air gas engine. According to an embodiment, the high-pressure air gas engine is a high-pressure ambient air or oxygen source controlled by a proportional valve.

According to an embodiment, the inhalation pathway is configured such that when a blockage occurs in the exhalation pathway, mechanical ventilation of the patient's lungs is possible.

According to an embodiment, the dynamic blower is a dynamically controlled centrifugal blower.

According to an embodiment, the exhalation pathway further comprises a bi-directional flow sensor.

According to an embodiment, the inhalation pathway comprises at least one proportional valve.

According to an embodiment, the inhalation pathway comprises a blower bypass valve, the blower bypass valve configured to bypass the blower during exhalation when there is a blockage in the exhalation pathway, wherein the blower is a constant speed blower.

According to an embodiment, the exhalation pathway comprises a dynamic blower configured to provide ambient air at pressure drawn from the exhalation port when a blockage occurs in the inhalation pathway.

According to an embodiment, the emergency valve is a bi-directional safety valve.

According to an embodiment, the emergency valve is an inspiratory hold valve.

According to an aspect is a ventilator system configured to enable breathing in the event of a blockage. The system includes: (i) a bi-directional emergency valve in an inhalation pathway of the ventilator system; and (ii) one or more controllers configured to: detect a blockage in the inhalation pathway and/or an exhalation pathway of the ventilator system; operate a blower in the inhalation pathway; and operate the emergency valve; wherein, upon detecting a blockage in the inhalation pathway, the one or more controllers are configured to open the bi-directional exhalation valve to allow the patient to draw air from an exhalation port of the exhalation pathway; and wherein, upon detecting a blockage in the exhalation pathway, the one or more controllers are configured to direct the blower to deliver inhalant to the patient during inhalation, and further configured to direct the blower to stop delivering inhalant to the patient during exhalation and to open the bi-directional emergency valve such that exhalant exits the ventilator through the bi-directional emergency valve and the blower.

According to an embodiment, during exhalation the exhalant exits the ventilator through the bi-directional exhalation valve and the exhalation port of the exhalation pathway.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a ventilator system and method. More generally, Applicant has recognized and appreciated that it would be beneficial to provide a ventilator system and method that allows a patient to breathe even in the occurrence of a blockage in either the gas delivery path or the gas return path. For example, the ventilator system comprises an inhalation pathway with an ambient air inlet, a bi-directional emergency valve such as a safety valve or inspiratory hold valve, and a dynamic blower. The ventilator system also includes an exhalation pathway with a bi-directional exhalation valve and an exhalation port. When a blockage occurs in the inhalation pathway, during inspiration ambient air can be drawn by the patient from the exhalation port and through the bi-directional exhalation valve, and during exhalation exhalant exits the ventilator through the bi-directional exhalation valve and the exhalation port. When a blockage occurs in the exhalation pathway, during inspiration inhalant is delivered to the patient by the dynamic blower, and during exhalation the dynamic blower lowers its speed or stops, and the exhalant exits the ventilator through the bi-directional emergency valve, the dynamic blower, and the ambient air inlet.

The ventilator system and method disclosed or otherwise envisioned herein provides numerous advantages over the prior art. Providing a ventilator that enables exhalation through an inhalation pathway in the event of a blockage in an exhalation pathway, and enables inhalation from an exhalation pathway in the event of a blockage in an inhalation pathway, allows a patient to breathe even in the occurrence of a blockage, thereby improving patient outcomes.

Figure 1:
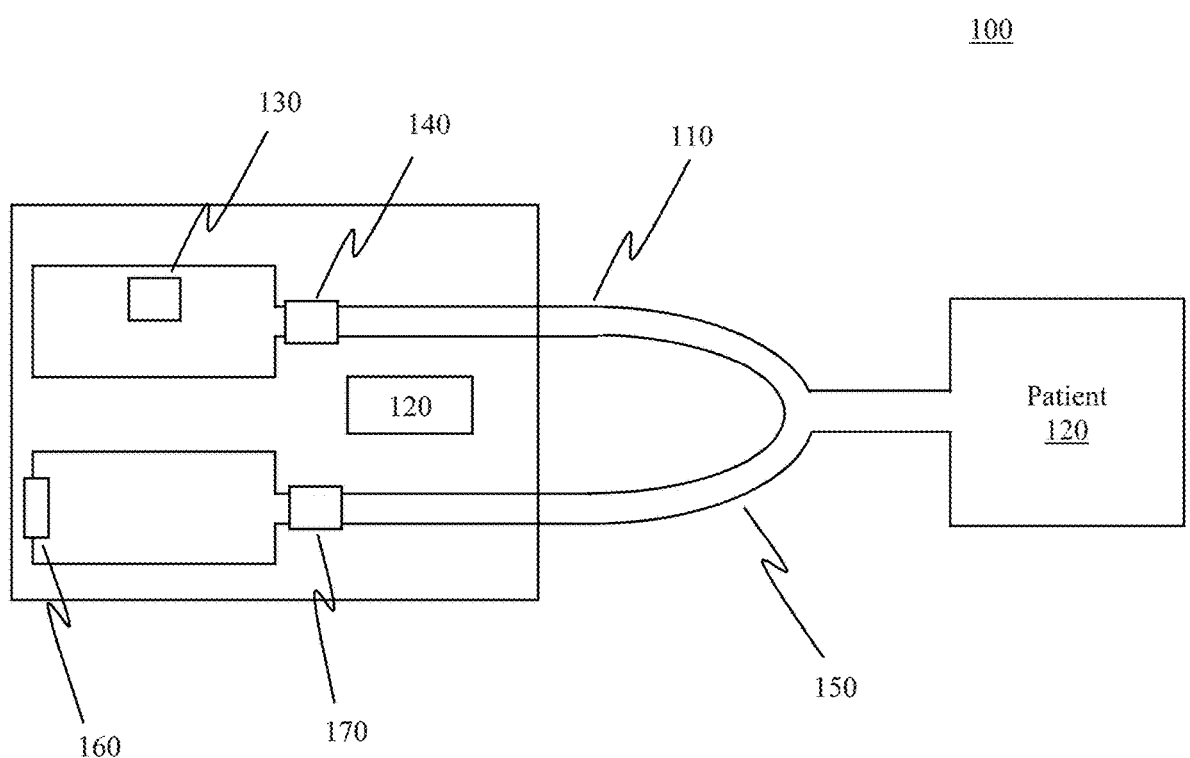
FIG. 1 is a schematic representation of a prior art ventilator system.

Referring to FIG. 1, in one embodiment, is a block diagram of a prior art dual-limb ventilation system 100. The system includes an inhalation pathway 110 through which inhalant is provided to the patient 120. The inhalant is any gas, including but not limited to ambient air and oxygen, among others. According to an embodiment, the ventilation system 100 comprises a unidirectional ambient air blower 130 as an air source, and may also comprise oxygen from a pressurized oxygen source. The inhalation pathway 110 also includes, among many other possible elements such as an air flow sensor (not shown), an inspiratory check valve 140 configured to prevent exhalant from entering further into the inhalation pathway. The inspiratory check valve 140 thereby prevents, for example, rebreathing of exhalant and also prevents cross-contamination of gas source (ambient air and $O_2$) gas delivery paths. Although the inspiratory check valve and blower are shown at particular locations along the inhalation pathway, it should be understood that their location is highly adaptable and can be at many different locations along the inhalation pathway.

The prior art dual-limb ventilation system 100 also comprises an exhalation pathway 150 through which exhalant is received from the patient 120 and exits the exhalation pathway via an exhalation port 160. The exhalation pathway 150 also includes, among many other possible elements such as an air flow sensor (not shown), an exhalation check valve 170 configured to prevent inhalation through the exhalation port. Although exhalation check valve 170 is shown at a particular location along the exhalation pathway, it should be understood that its location is highly adaptable and can be at many different locations along the exhalation pathway.

According to an embodiment, the system also includes a controller 120, which is a conventional microprocessor, an application specific integrated circuit (ASIC), a system on chip (SOC), and/or a field-programmable gate arrays (FPGA), among other types of controllers. A controller may be implemented with or without employing a processor, and also may be implemented as a combination of dedicated hardware to perform some functions and a processor (e.g., one or more programmed microprocessors and associated circuitry) to perform other functions.

The controller 120 can be coupled with or otherwise in communication with any needed memory, power supply, I/O devices, control circuitry, sensors, valves, blowers, and/or other devices necessary for operation of the ventilator according to the embodiments described or otherwise envisioned herein. For example, in various implementations, a processor or controller may be associated with one or more storage media. In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

According to an embodiment, the controller 120 is configured or programmed to function as a blower controller to coordinate and control the blower functions of the ventilator. For example, the blower controller can control the rate and strength of the blower(s) of the system, thereby controlling or directing the flow through the circuit, and the speed and thus the pressure at its outlet, or the flow out of the outlet port. According to another embodiment, the blower controller is a separate component, preferably in communication with controller 120, although the multiple functions of the system can be otherwise coordinated. Although this embodiment uses the blower flow controller to excite the circuit, any type of flow source, including for example proportionally controlled compressed gas valves, could be utilized where the source provides a means of actual flow and pressure measurements.

According to this prior art embodiment, if an occlusion occurs in the inspiratory gas path 110 such as in the limb of the tubing system, the patient will be able to exhale the gas in their lungs through the exhalation port 160, but will not be able to draw air from the atmosphere as the exhalation check valve 170 intentionally blocks the ingress of fresh gas into the tubing.

Similarly, if an occlusion occurs in the exhalation limb 150, the patient will not be able to relieve the pressure in their lungs since the exhalation port 160 is not available and the inspiratory check valve 140 intentionally prevents gas from escaping through the inspiratory gas path 110.

In either case, the pressure in the tubing system will elevate to the relief level required for a pressure relief valve (not shown) to begin limiting the pressure. An alarm for the occlusion will issue, and a clinical person will have to resolve the problem. If the patient does not receive prompt attention, they may be injured or asphyxiate.

Figure 2:
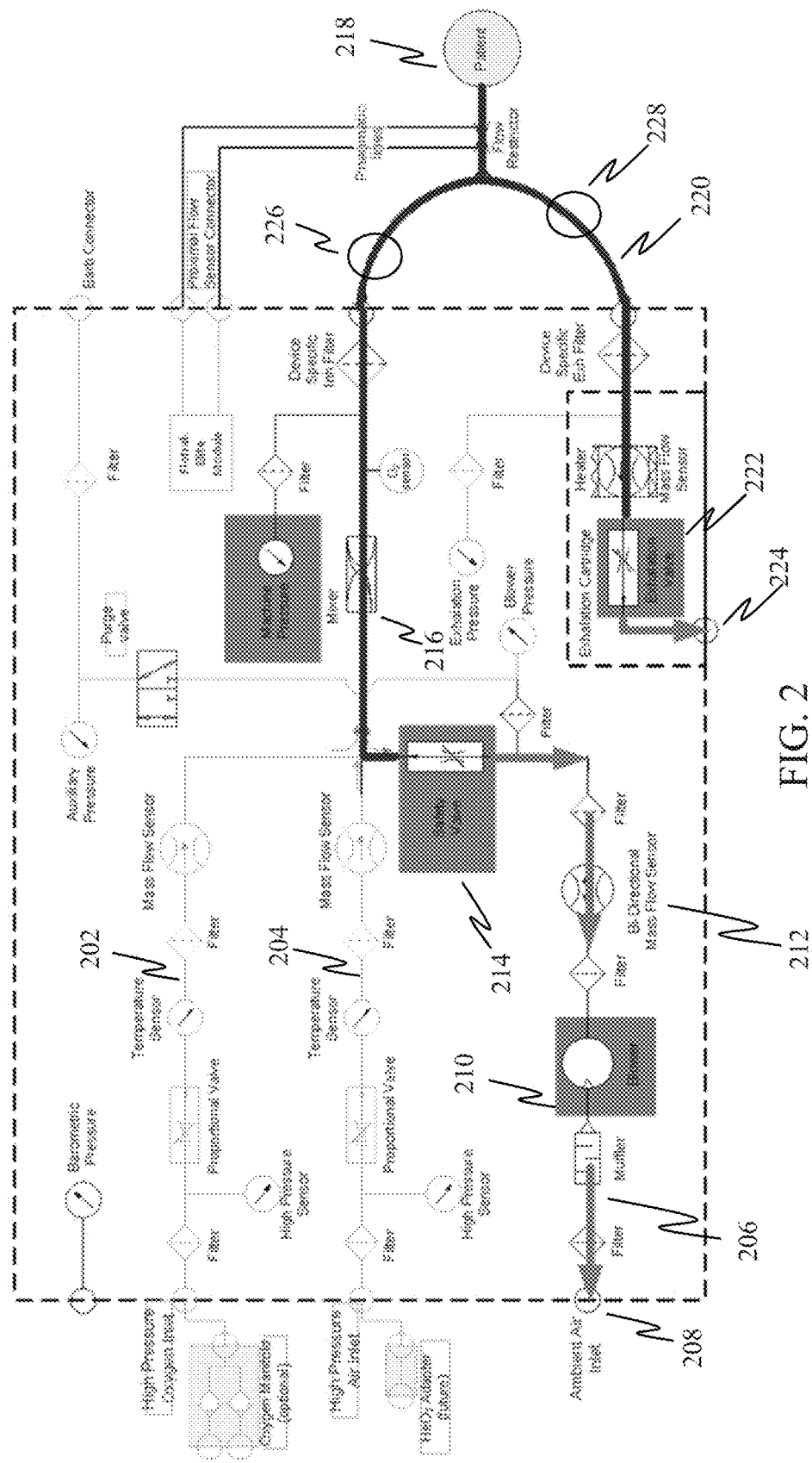
FIG. 2 is a schematic representation of a ventilator system, in accordance with an embodiment.

Referring to FIG. 2, in accordance with an embodiment, is a schematic representation of a novel ventilator system 200. The system includes an inhalation pathway comprising three components: (1) a high pressure oxygen component 202 with a high pressure oxygen inlet and one or more other components such as a proportional valve and a flow sensor; (2) a high pressure air component 204 with a high pressure air inlet and one or more other components such as a proportional valve and a flow sensor; and (3) an ambient air component 206 with an ambient air inlet 208, a dynamically-controlled centrifugal blower 210, a bi-directional flow sensor 212, a bi-directional emergency valve 214 such as a safety valve, and optionally other components. Notably, although the inhalation pathway of ventilator system 200 comprises three gas delivery engines in this particular embodiment, the system may comprise fewer or additional gas delivery engines. The inhalation pathway further comprises a mixer 216 configured to receive the gas input from each of the three components of the inhalation pathway, mix the gas input, and provide it to the patient 218.

Ventilator system 200 further comprises an exhalation pathway 220 via which exhalant is allowed to be exhaled from the patient 218 to the exhalation port 224. The exhalation pathway 220 comprises one or more additional components, such as for example, a flow sensor and a bi-directional exhalation valve 222, among other possible components.

Notably, ventilator system 200 is lacking the unidirectional inhalation check valve and the unidirectional exhalation check valve found in prior art ventilator systems. As described in detail below, this is an important aspect of the novel ventilator system 200 that enables the system to prevent asphyxia in the event of a blockage in either the inhalation pathway or the exhalation pathway.

During normal inhalation, one or both proportional valves in the high-pressure pathways open to allow high-pressure gas to enter the system, and blower 210 forces ambient air into the system. The mixer 216 receives the gases and generates the proper mix which is then provided at pressure to patient 218 for inhalation. During normal exhalation, the one or both proportional valves in the high-pressure pathways close and blower 210 lowers its speed or stops, and no gas is provided to the patient. The exhalant is allowed to exit via the exhalation pathway, through the exhalation valve 222 and the exhalation port 224.

Ventilator system 200 is configured to enable breathing by patient 218 in the event of a blockage or occlusion in either the inhalation pathway or the exhalation pathway. In the event of a blockage along the inhalation pathway, such as at location 226 or any other location along the inhalation pathway, gas can no longer be provided to patient 218 from the one or more high-pressure gas sources or the ambient air source. The blockage along the inhalation pathway may be caused, for example, by a tubing circuit obstruction or the exhalation valve getting stuck closed. The inhalant in the patient's lungs at the time of the blockage can exit via the exhalation pathway per normal, but without the design of the ventilator system 200 the patient would not be able to receive new gas. The ventilator system will detect the blockage due to the flow sensors in the inhalation pathway no longer detecting flow, and the system will raise an alarm, but in prior art systems the issue may not be resolved in enough time to prevent injury or asphyxiation. Accordingly, the exhalation pathway is configured with a bi-directional exhalation valve 222 that enables the patient 218 to draw ambient air in reverse along the exhalation pathway, from exhalation port 224 through the bi-directional exhalation valve 222 and into the lungs of patient 218. Similarly, the patient can exhale via the exhalation pathway per normal. Although inhalant is not provided to the patient under pressure, even minimal self-initiated inhalation by the patient will allow enough oxygen to enter the patient's lungs to prevent serious injury or asphyxia.

According to an embodiment, the exhalation pathway may comprise a dynamically controlled blower configured to provide ambient air from the exhalation port 224 to the patient in the event of a blockage in the inhalation pathway.

When a blockage in the inhalation pathway is detected by the ventilator system, the blower can be controlled to provide ambient air from the exhalation port 224 to the patient during an inhalation phase, and controlled to lower or stop the blower speed during an exhalation phase. According to a further embodiment of a blower in the exhalation pathway, the exhalation pathway may further comprise an open/closed valve to block the blower path in normal operation and avoid gas leakages through the blower when it is inactive. Many other variations are possible.

In the event of a blockage along the exhalation pathway, such as at location 228 or any other location along the exhalation pathway, gas can still be provided to patient 218 from the one or more high-pressure gas sources and the ambient air source, but the patient cannot exhale via the exhalation pathway. Thus, in normal ventilator systems the exhalant in the patient's lungs at the time of the blockage would not be able to exit the ventilator system and new gas could not be provided to the patient. The ventilator system will detect the blockage due to the flow sensors in the inhalation pathway no longer detecting flow, and/or the flow sensors in the exhalation pathway no longer detecting flow, and the system will raise an alarm, but in prior art systems the issue may not be resolved in enough time to prevent injury or asphyxiation. Accordingly, the inhalation pathway is configured with a blower 210, bi-directional sensor 212, and bi-directional safety valve 214. Thus, when the blockage occurs in the exhalation pathway, the system detects the lack of flow and the exhalant in the patient's lungs at the time of the blockage in the exhalation pathway. The blower 210 lowers its speed or stops and the exhalant is allowed to exit the ambient air component 206 of the inhalation pathway, via the bi-directional safety valve 214, the bi-directional flow sensor 212, the blower 210, and the ambient air inlet 208 which is functioning as an outlet. At the end of an exhalation, the blower 210 and the proportional valve(s) can activate to provide pressurized air to the patient via the inhalation pathway as per normal.

Figure 3:
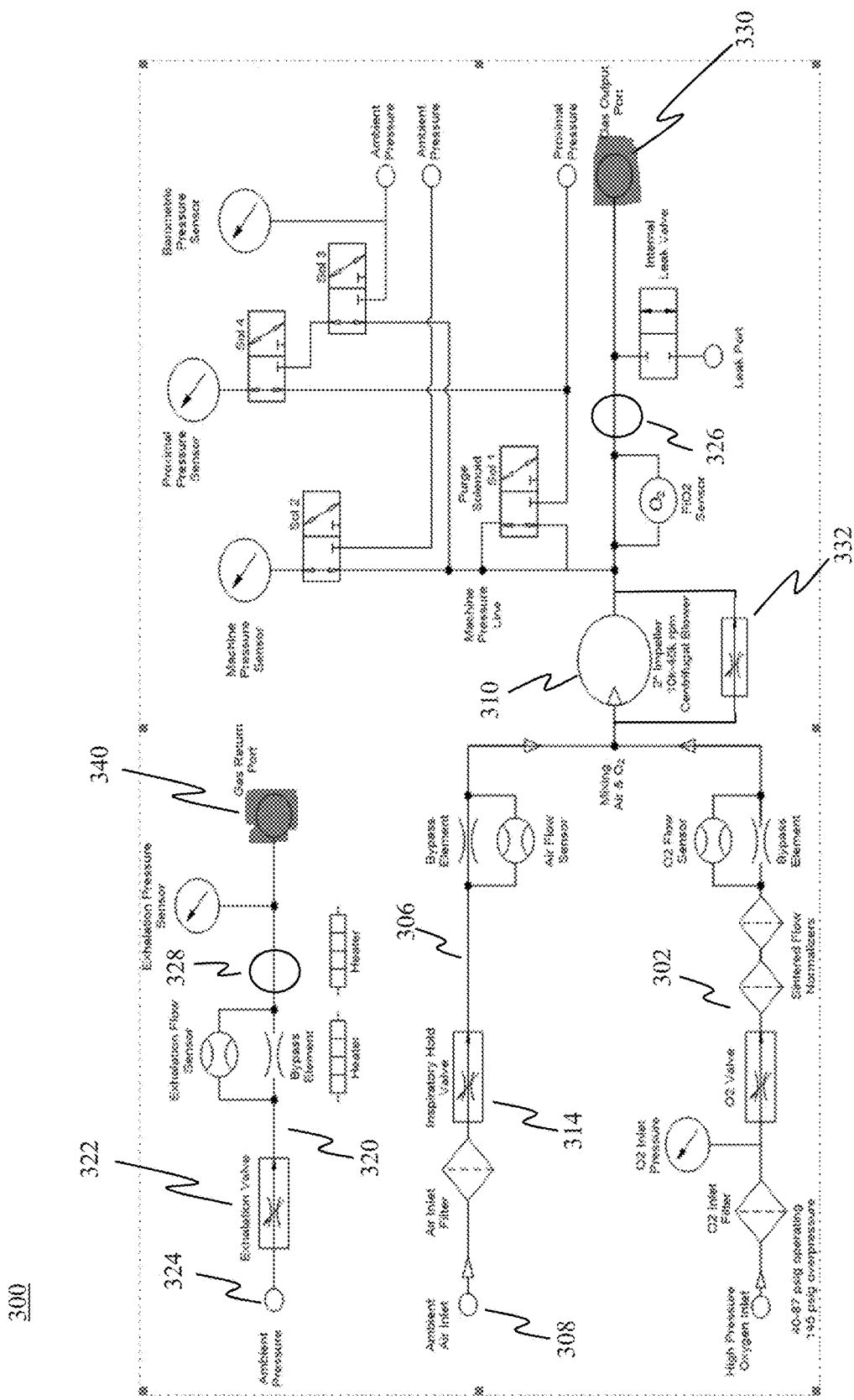
FIG. 3 is a schematic representation of a ventilator system, in accordance with an embodiment.

According to an embodiment shown in FIG. 3, the inhalation pathway comprises a blower bypass valve 332 configured to bypass the blower in the event of an occlusion. In this embodiment the blower may be dynamically controlled or may be controlled to provide a constant speed. In the event of an occlusion in the exhalation pathway, the blower bypass valve can function to produce an inhalation phase and an exhalation phase through the inhalation pathway. For example, the blower bypass valve can be opened or closed, depending on the configuration, during inhalation so that the constant speed blower can provide inhalant to the patient. During exhalation through the inhalation pathway due to occlusion in the exhalation pathway, the blower bypass valve can be opened or closed, depending on the configuration, to bypass the constant speed blower and allow exhalation through the inhalation pathway.

Referring to FIG. 3, in accordance with an embodiment, is a schematic representation of a novel ventilator system 300. The system includes an inhalation pathway comprising two components: (1) a high-pressure oxygen component 302 with a high pressure oxygen inlet and one or more other components such as an $O_2$ valve and a flow sensor; and (2) an ambient air component 306 with an ambient air inlet 308, an emergency valve 314 such as an inspiratory hold valve, and optionally other components. Notably, although the inhalation pathway of ventilator system 300 comprises two gas delivery engines in this particular embodiment, the system may comprise fewer or additional gas delivery engines. The inhalation pathway of ventilator system 300 further comprises a dynamically controlled centrifugal blower 310, which in this particular embodiment is downstream of a mixer for the high-pressure oxygen component 302 and the ambient air component 306. The inhalation pathway leads to a gas output port 330 that leads to a patient (not shown).

Ventilator system 300 further comprises an exhalation pathway 320 which receives exhalant from the patient via the gas return port 340 and flows to the exhalation port 324. The exhalation pathway 320 comprises one or more additional components, such as for example, a flow sensor and a bi-directional exhalation valve 322, among other possible components.

Notably, ventilator system 300 is lacking the unidirectional inhalation check valve and the unidirectional exhalation check valve found in prior art ventilator systems. As described in detail below, this is an important aspect of the novel ventilator system 300 that enables the system to prevent asphyxia in the event of a blockage in either the inhalation pathway or the exhalation pathway.

During normal inhalation, the $O_2$ valve in the high-pressure pathway opens to allow high-pressure gas to enter the system, the inspiratory hold valve 314 allows the flow of air from the air inlet 308 into the system, the gases are mixed either by a mixer or via control of the $O_2$ valve and the air and $O_2$ sensors, and the blower 310 forces the mixed gases to the patient via the gas output port 330. During normal exhalation, the $O_2$ valve in the high-pressure pathway closes and the inspiratory hold valve 314 prevents the flow of air from the air inlet 308 into the system and blower 310 lowers its speed or stops, and no gas is provided to the patient. The exhalant is allowed to exit via the exhalation pathway, from the patient to gas return port 340 through the exhalation valve 322 and the exhalation port 324.

Ventilator system 300 is configured to enable breathing by the patient in the event of a blockage or occlusion in either the inhalation pathway or the exhalation pathway. In the event of a blockage along the inhalation pathway, such as at location 326 or any other location along the inhalation pathway, gas can no longer be provided to the patient from the high-pressure gas source or the ambient air source. The blockage along the inhalation pathway may be caused, for example, by a tubing circuit obstruction. The inhalant in the patient's lungs at the time of the blockage can exit via the exhalation pathway per normal, but without the design of the ventilator system 300 the patient would not be able to receive new gas. The ventilator system will detect the blockage using the flow sensors in the inhalation pathway no longer detecting flow or insufficient flow, and the system will raise an alarm, but in prior art systems the issue may not be resolved in enough time to prevent injury or asphyxiation. Accordingly, the exhalation pathway is configured with a bi-directional exhalation valve 322 that enables the patient to draw ambient air in reverse along the exhalation pathway, from exhalation port 324 through the bi-directional exhalation valve 322 and into the lungs of the patient. Similarly, the patient can exhale via the exhalation pathway per normal. Although inhalant is not provided to the patient under pressure, even minimal self-initiated inhalation by the patient will allow enough oxygen to enter the patient's lungs to delay serious injury or asphyxia, allowing the caregiver to resolve the problem. Further, as described above, according to one embodiment, the exhalation pathway may comprise a dynamically controlled blower configured to provide ambient air from the exhalation port 224 to the patient in the event of a blockage in the inhalation pathway.

Notably, according to an embodiment, a blockage such as an occlusion in either the inhalation pathway or the exhalation pathway may not be a total blockage. Instead, the blockage may be partial but severe enough to impede proper respiration and thus could result in asphyxiation or other serious injuries. Accordingly, the alternate flow pathways described or otherwise envisioned herein may be implemented in the event of a partial blockage. The ventilator system can be programmed, designed, or configured such that there is a threshold level of flow or pressure, ranging from no flow or pressure to a predetermined, experimentally derived, or programmed level of flow or pressure, that triggers the alternate flow pathways described or otherwise envisioned herein.

In the event of a blockage along the exhalation pathway, such as at location 328 or any other location along the exhalation pathway, gas can still be provided to the patient from the high-pressure gas source and the ambient air source, but the patient cannot exhale via the exhalation pathway. Thus, in normal ventilator systems the exhalant in the patient's lungs at the time of the blockage would not be able to exit the ventilator system and new gas could not be provided to the patient. The ventilator system will detect the blockage using information conveyed by one or more of the flow and pressure sensors that monitor ventilation activity in the machine, and/or the flow sensors in the exhalation pathway no longer detecting flow, and the system will raise an alarm, but in prior art systems the issue may not be resolved in enough time to prevent injury or asphyxiation. Accordingly, the inhalation pathway is configured with a blower 310 and a bi-directional inspiratory hold valve 314. Thus, when the blockage occurs in the exhalation pathway, the system detects the lack of flow and the exhalant in the patient's lungs at the time of the blockage in the exhalation pathway. The blower 310 lowers its speed or stops and the exhalant is allowed to exit the ambient air component 306 of the inhalation pathway, via the blower 310 and the bi-directional inspiratory hold valve 314, and out the ambient air inlet 308 which is functioning as an outlet. At the end of an exhalation, the blower 310 and the inhalation valve(s) can activate to provide pressurized air to the patient via the inhalation pathway as per normal. Accordingly, the inspiratory hold valve 314 can be controlled to allow or block gas ingress.

Notably, both ventilator systems 200 and 300 are capable of mechanical ventilation of the patient's lungs in at least the case of a blockage of the exhalation gas path. Other mechanisms may be provided to allow mechanical ventilation when the exhalation gas path is blocked via provision of auxiliary valves controlled by the ventilator control center.

Figure 4:
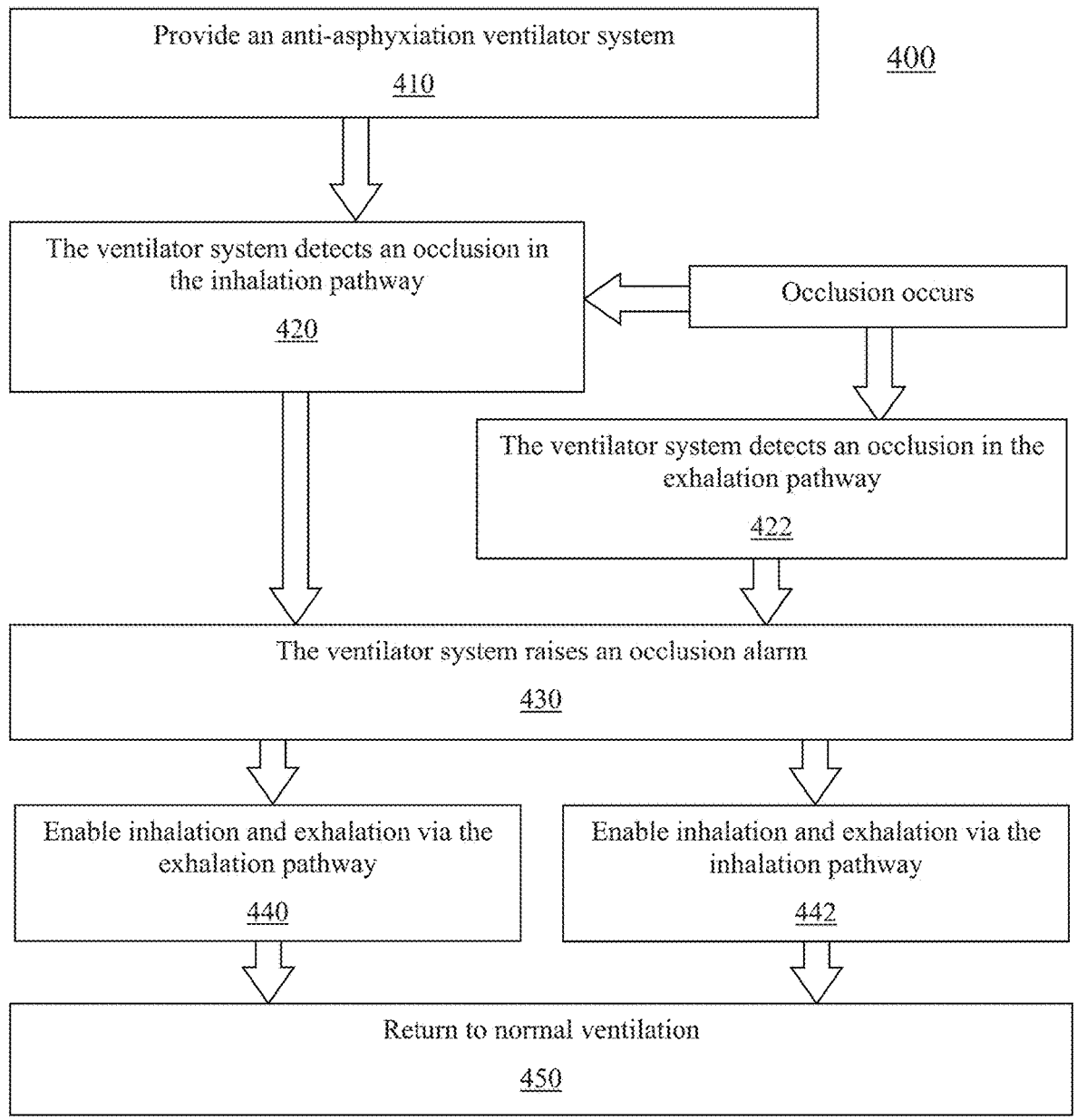
FIG. 4 is a flowchart of a method for enabling breathing during an occlusion in an anti-asphyxiation ventilator system, in accordance with an embodiment.

Referring to FIG. 4, in one embodiment, is a flowchart of a method 400 for enabling a patient to breathe even in the occurrence of a blockage in either the gas delivery path or the gas return path, thereby preventing oxygen deprivation injuries or asphyxiation. At step 410 of the method, an anti-asphyxiation ventilator system is provided. The anti-asphyxiation ventilator system can be any of the embodiments described or otherwise envisioned herein.

At some point during operation of the ventilator, an occlusion inadvertently occurs in either the inhalation pathway or the exhalation pathway. The anti-asphyxiation ventilator system detects the occlusion and adapts in order to allow the patient an opportunity to breathe despite the occlusion.

At step 420, there is an occlusion in the inhalation pathway of the anti-asphyxiation ventilator system, and gas can no longer be provided to patient 218 from the one or more high-pressure gas sources or the ambient air source. The inhalant in the patient's lungs at the time of the blockage can exit via the exhalation pathway per normal, but without the design of the anti-asphyxiation ventilator system the patient would not be able to receive new gas. At step 420, the anti-asphyxiation ventilator system detects the blockage due to the flow sensors in the inhalation pathway no longer detecting flow or detecting insufficient flow.

At step 430, the system raises an alarm to alert a healthcare facility and/or professional to the existence of the occlusion.

At step 440, with an occlusion in the inhalation pathway, the anti-asphyxiation ventilator system enables both inhalation and exhalation via the exhalation pathway. For example, the exhalation pathway is configured with a bi-directional exhalation valve that enables the patient to draw ambient air in reverse along the exhalation pathway, from an exhalation port through the bi-directional exhalation valve and into the lungs of the patient. Similarly, the patient can exhale via the exhalation pathway per normal. Although inhalant is not provided to the patient under pressure, even minimal self-initiated inhalation by the patient will allow enough oxygen to enter the patient's lungs to prevent or delay serious injury or asphyxia.

At step 442, with an occlusion in the exhalation pathway, the anti-asphyxiation ventilator system enables both inhalation and exhalation via the inhalation pathway. For example, the inhalation pathway is configured with at least a blower and a bi-directional safety valve or inspiratory hold valve. Thus, when the blockage occurs in the exhalation pathway, the system detects the lack of flow and the exhalant in the patient's lungs at the time of the blockage in the exhalation pathway. The blower lowers its speed or stops, and the exhalant is allowed to exit the ambient air component of the inhalation pathway, via the blower and the bi-directional safety valve or inspiratory hold valve. At the of an exhalation, the blower and proportional valve(s) can activate to provide pressurized air to the patient via the inhalation pathway as per normal.

At step 450, the occlusion has been resolved by a clinician, the anti-asphyxiation ventilator system detects the normal flow of air and the system returns to normal ventilation operation.

Accordingly, the ventilator system and method disclosed or otherwise envisioned herein provides numerous advantages over the prior art. Providing a ventilator that enables exhalation through an inhalation pathway in the event of a blockage in an exhalation pathway, and enables inhalation from an exhalation pathway in the event of a blockage in an inhalation pathway, allows a patient to breathe even in the occurrence of a blockage, thereby improving patient outcomes.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A ventilator system configured to enable breathing in the event of a blockage, comprising:
    an inhalation pathway comprising an ambient air inlet, a bi-directional emergency valve, and a blower;
    an exhalation pathway comprising a bi-directional exhalation valve and an exhalation port;
    wherein the exhalation pathway is configured such that when a blockage occurs in the inhalation pathway, during inspiration breathable air can be drawn by a patient from the exhalation port and through the bi-directional exhalation valve, and during exhalation exhaled air from the patient exits the ventilator system through the bi-directional exhalation valve and the exhalation port;
    wherein the inhalation pathway is configured such that when a blockage occurs in the exhalation pathway, during inspiration breathable air is delivered to the patient by the blower, and during exhalation the blower lowers its speed or stops delivering breathable air to the patient and the exhaled air from the patient exits the ventilator system through the bi-directional emergency valve, the blower, and the ambient air inlet.

2. The ventilator system of claim 1, wherein the inhalation pathway further comprises a bi-directional ambient air flow sensor.

3. The ventilator system of claim 1, wherein the inhalation pathway comprises an ambient air gas engine and a high-pressure gas engine.

4. The ventilator system of claim 3, wherein the inhalation pathway further comprises a high-pressure air gas engine.

5. The ventilator system of claim 1, wherein the inhalation pathway is configured such that when a blockage occurs in the exhalation pathway, mechanical ventilation of the patient's lungs is possible.

6. The ventilator system of claim 1, wherein the blower is a dynamically controlled centrifugal blower.

7. The ventilator system of claim 1, wherein the inhalation pathway comprises a blower bypass valve, the blower bypass valve configured to bypass the blower during exhalation when there is a blockage in the exhalation pathway, wherein the blower is a constant speed blower.

8. The ventilator system of claim 1, wherein the exhalation pathway comprises a dynamic blower configured to provide ambient air at pressure drawn from the exhalation port when a blockage occurs in the inhalation pathway.

9. The ventilator system of claim 1, wherein the emergency valve is a bi-directional safety valve.

10. The ventilator system of claim 1, wherein the emergency valve is an inspiratory hold valve.

11. The ventilator system of claim 1, wherein the inhalation pathway lacks a unidirectional inhalation check valve.

12. The ventilator system of claim 1, wherein the exhalation pathway lacks a unidirectional exhalation check valve.

13. A ventilator system configured to enable breathing in the event of a blockage, comprising:
    a bi-directional emergency valve in an inhalation pathway of the ventilator system; and
    one or more controllers configured to:
    detect a blockage in the inhalation pathway and/or an exhalation pathway of the ventilator system;

operate a blower in the inhalation pathway; and
operate the bi-directional emergency valve;
wherein, upon detecting a blockage in the inhalation pathway, the one or more controllers are configured to open a bi-directional exhalation valve to allow a patient to draw air from an exhalation port of the exhalation pathway; and
wherein, upon detecting a blockage in the exhalation pathway, the one or more controllers are configured to direct the blower to deliver air to the patient during inhalation, and further configured to direct the blower to lower its speed or stop delivering air during exhalation and to open the bi-directional emergency valve such that exhaled air from the patient exits the ventilator system through the bi-directional emergency valve and the blower.

14. The ventilator system of claim 13, wherein the blower is a dynamically controlled centrifugal blower.

15. The ventilator system of claim 13, wherein the inhalation pathway is configured such that when a blockage occurs in the exhalation pathway, mechanical ventilation of the patient's lungs is possible.

16. The ventilator system of claim 13, wherein during exhalation exhaled air from the patient exits the ventilator system through the bi-directional exhalation valve and the exhalation port of the exhalation pathway.

17. The ventilator system of claim 13, wherein the inhalation pathway comprises an ambient air gas engine and a high-pressure gas engine.

18. The ventilator system of claim 13, wherein the inhalation pathway lacks a unidirectional inhalation check valve.

19. The ventilator system of claim 13, wherein the exhalation pathway lacks a unidirectional exhalation check valve.

20. A method of enabling breathing via a ventilation system if a blockage occurs in an inhalation pathway or an exhalation pathway, comprising:
configuring the inhalation pathway with a blower and without a unidirectional inhalation check valve;
configuring the exhalation pathway without a unidirectional exhalation check valve;
after a blockage occurs in the inhalation pathway:
during inspiration, using a bi-directional exhalation valve of the exhalation pathway to allow a patient to draw air from an exhalation port and through the bi-directional exhalation valve, wherein gas flow of the exhalation pathway is unobstructed between the patient and the bi-directional exhalation valve; and
during exhalation, using the bi-directional exhalation valve and the exhalation port to allow exhaled air to be expelled; and
after a blockage occurs in the exhalation pathway:
during inspiration, delivering air via the inhalation pathway; and
during exhalation, using a bi-directional emergency valve of the inhalation pathway to allow exhaled air from the patient to be expelled, wherein gas flow of the inhalation pathway is unobstructed between the patient and the bi-directional emergency valve.

* * * * *